(12) United States Patent
Holmaas et al.

(10) Patent No.: US 7,754,920 B1
(45) Date of Patent: Jul. 13, 2010

(54) SOLVENT REDUCTION IN CRYSTALLISATION OF INTERMEDIATE FOR NON-IONIC X-RAY CONTRAST AGENTS

(75) Inventors: Lars Terje Holmaas, Spangereid (NO); Kristin Rypestol, Mandal (NO)

(73) Assignee: GE HealthCare AS, Oslo (NO)

( * ) Notice: Subject to any disclaimer, the term of this patent is extended or adjusted under 35 U.S.C. 154(b) by 0 days.

(21) Appl. No.: 12/620,650

(22) Filed: Nov. 18, 2009

Related U.S. Application Data

(60) Provisional application No. 61/227,090, filed on Jul. 21, 2009.

(51) Int. Cl.
*C07C 233/00* (2006.01)
(52) U.S. Cl. .................. 564/218; 564/219; 564/220
(58) Field of Classification Search .................. None
See application file for complete search history.

(56) References Cited

U.S. PATENT DOCUMENTS

| | | | |
|---|---|---|---|
| 5,349,085 A | * | 9/1994 | Hansen et al. ............. 564/153 |
| 5,840,967 A | | 11/1998 | Gulbrandsen et al. |
| 6,974,882 B2 | * | 12/2005 | Homestad ................. 564/153 |
| 2002/0010368 A1 | * | 1/2002 | Homestad ................. 564/153 |
| 2008/0161606 A1 | * | 7/2008 | Homestad ................. 564/153 |
| 2009/0112022 A1 | * | 4/2009 | Homestad ................. 564/153 |

FOREIGN PATENT DOCUMENTS

KR 2003032185 * 4/2003

* cited by examiner

*Primary Examiner*—Karl J Puttlitz

(57) ABSTRACT

This invention relates to an improved method for crystallizing 5-acetamido-N,N'-bis(2,3-dihydroxypropyl)-2,4,6-triiodo-isophthalamide ("Compound A"), an intermediate in the industrial preparation of non-ionic X-ray contrast agents. In particular, the present invention provides an industrial process for crystallization of Compound A by evaporating methanol and water from the mother liquor after an initial crystallization of Compound A following the acetylation reaction. Specifically, the mother liquor is maintained at more than about 75% (v/v) of water and less than about 25% (v/v) of alcoholic solvent.

2 Claims, No Drawings

SOLVENT REDUCTION IN CRYSTALLISATION OF INTERMEDIATE FOR NON-IONIC X-RAY CONTRAST AGENTS

CROSS REFERENCE TO RELATED APPLICATIONS

The present application claims benefit of priority under 35 U.S.C. §119(e) to U.S. Provisional Application No. 61/227,090 filed Jul. 21, 2009, the entire disclosure of which is hereby incorporated by reference.

TECHNICAL FIELD

This invention relates generally to large-scale synthesis of non-ionic X-ray contrast agents. It further relates to an improved method for crystallising 5-acetamido-N,N-bis(2,3-dihydroxypropyl)-2,4,6-triiodoisophthalamide ("Compound A"), an intermediate in the industrial preparation of non-ionic X-ray contrast agents. In particular, it relates to reducing the volume percentage of methanol in the mother liquor following an initial crystallisation of Compound A.

BACKGROUND OF THE INVENTION

Non-ionic X-ray contrast agents constitute a very important class of pharmaceutical compounds produced in large quantities. 5-[N-(2,3-dihydroxypropyl)-acetamido]-N,N'-bis(2,3-dihydroxypropyl)-2,4,6-triiodo-isophthalamide ("iohexyl"), 5-[N-(2-hydroxy-3-methoxypropyl)acetamido]-N,N'-bis(2,3-dihydroxypropyl)-2,4,6-triiodo-isophthalamide ("iopentol") and 1,3-bis(acetamido)-N,N'-bis[3,5-bis(2,3-dihydroxypropyl-aminocarbonyl)-2,4,6-triiodophenyl]-2-hydroxypropane ("iodixanol") are important examples of such compounds. These compounds generally contain one or two triiodinated benzene rings.

In particular, iodixanol, marketed under the trade name Visipaque®, is one of the most used agents in diagnostic X-ray procedures. It is produced in large quantities by GE Healthcare in Lindesnes, Norway. The industrial production of iodixanol involves a multistep chemical synthesis as shown in Scheme 1 below. See also U.S. Pat. No. 6,974,882. To reduce the cost of the final product, it is critical to optimize each synthetic step. Even a small improvement in reaction design can lead to significant savings in a large scale production.

The instant improvement is directed to the crystallisation of 5-acetylamino-N,N'-bis(2,3-dihydroxypropyl)-2,4,6-triiodoisophthalamide (Compound A) after the acetylation step, where 5-amino-N,N'-bis(2,3-dihydroxypropyl)-2,4,6-triiodoisophthalamide (Compound B) is acetylated to produce Compound A. According to the present invention, the concentration of methanol in the mother liquor following an initial crystallization of Compound A is significantly reduced to increase the crystallisation yield of Compound A.

Scheme 1

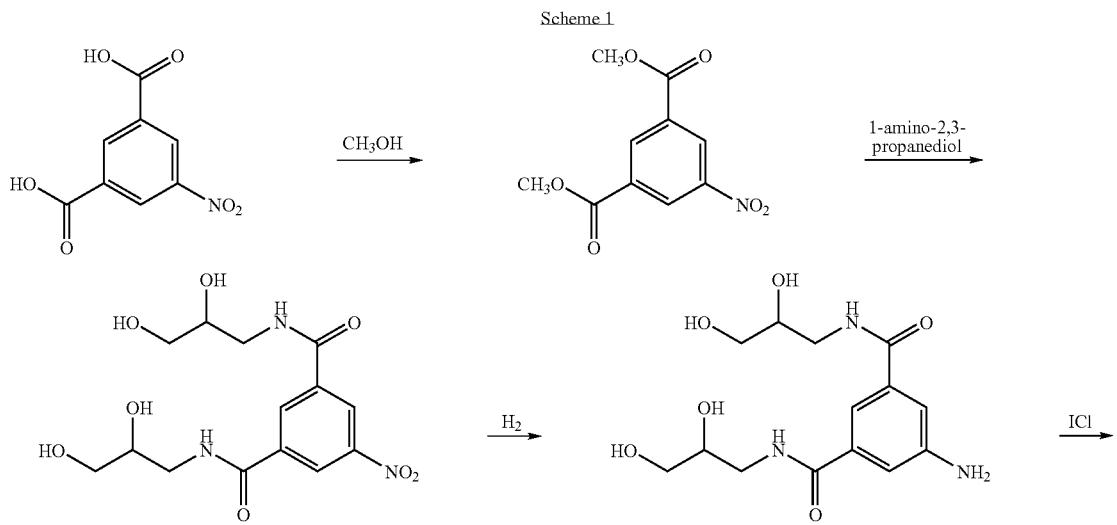

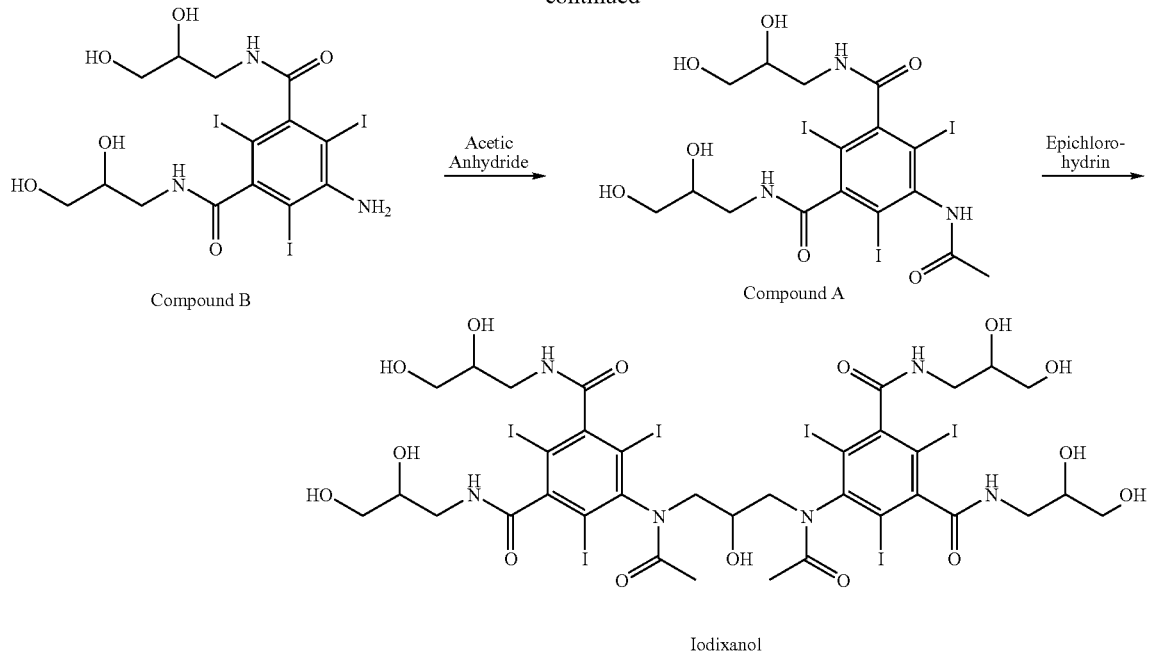

SUMMARY OF THE INVENTION

The present invention provides an industrial process for crystallisation of Compound A by reducing the methanol content in the mother liquor after an initial crystallisation of Compound A. Specifically, methanol and water are evaporated, leading to the mother liquor containing more than about 75% (v/v) of water and less than about 25% (v/v) of methanol. In a preferred embodiment, the mother liquor contains more than about 80% (v/v) of water and less than about 20% (v/v) of methanol.

DETAILED DESCRIPTION OF THE INVENTION

In the industrial preparation of non-ionic X-ray contrast agents, Compound B is acetylated with acetic anhydride to produce Compound A as shown in Scheme 2 below. Compound B is obtained after acetylation of the amino group and the hydroxyl groups followed by hydrolysis of the acetoxy groups formed.

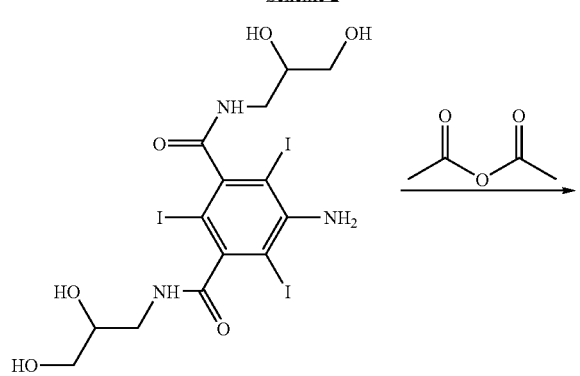

Scheme 2

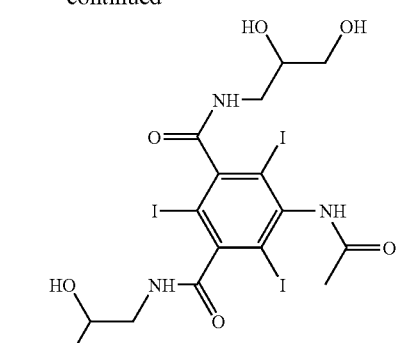

Typically, crude Compound A is crystallised from a mixture of water and methanol by addition of diluted hydrochloric acid. The pH is adjusted from about 12 to about 7 during crystallisation. Compound A crystallises when the pH reaches the point where the anionic form of Compound A (see figure below) is protonated, since neutral Compound A has a poor solubility in the water/methanol mixture. The solubility is also poor in the pure solvents, but

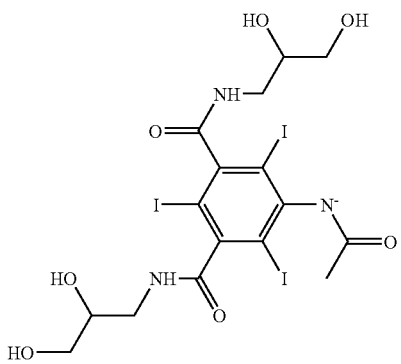

even more so in water than in methanol. The transition from deprotonated to neutral Compound A typically takes place at about pH 10-11.

The purification effect in the crystallisation is however dependent on the methanol content in the solution at the time of crystal formation. This means that even though the yield from the crystallisation process is maximised by increasing the water content in the crude mixture, water content, at a high level, will actually compromise the quality of the crystallised product. Thus, it has been commonly accepted that the alcoholic content at the time of crystal formation should be at least 25% to obtain the required purity of Compound A.

We have surprisingly found that methanol is much less critical after the crystals have been formed. Further growth on existing crystals gives the required purity even if the nature of the solvent has been altered. Thus, by decreasing methanol amount and increasing water content after crystal formation still gives the desired purity, but at the same time allows increased yield from the crystallisation step. Such decrease of methanol content may be obtained by evaporating a fraction of the mother liquor. For example, methanol may be reduced by distillation under slightly reduced pressure, since methanol is more volatile than water and hence is easier distilled off than water.

Another finding of the instant method is that the total volume of mother liquor is reduced without increasing the total solubility of Compound A in the mixture. This reduces the amount of dissolved Compound A in the mother liquor and thus increases the yield further without compromising the purity of the product.

In a preferred embodiment, the total amount of mother liquor may be reduced by as much as about 40% without detectable reduction in the resulting purity of Compound A. If the volume reduction is obtained by distillation at slightly reduced pressure (for example, pressures between about 0.2 and about 0.7 bar) the resulting water content in the mother liquor is at least 75-95%, more typically about 80-90%. A 40% reduction of the mother liquor volume typically increases the yield in the process from isolated Compound B to isolated Compound A by about 3%.

The invention is illustrated further by the following examples that are not to be construed as limiting the invention in scope to the specific procedures described in them.

EXAMPLES

Example 1

Ten experiments were made, each of which used two parallel crystallisers (reactors A and B) where one had mother liquor distilled off and one had not. The solutions of crude Compound A were in all cases made the following way.

Compound B was acetylated by a mixture of acetic anhydride and acetic acid (concentration about 91 v/v %, 2.0 L/kg Compound B) at 50-125° C. in the presence of catalytic amounts of p-toluene sulphonic acid. Excess acetic anhydride and acetic acid were distilled off under reduced pressure, and the resulting viscous solution diluted with methanol and water and hydrolysed by addition of aqueous sodium hydroxide at 50-60° C. to a stable pH of about 12. Hydrochloric acid (17.5 w/w %) was added to a pH of about 10.5-11.5 at 60° C. Then, seeds of crystalline Compound A (0.004 kg/kg Compound B) were added, and pH was further adjusted to 6.5-7.5 by hydrochloric acid (17.5 w/w %). At this stage the solvent composition was approximately 25% methanol and 75% water, with a total mother liquor volume of about 3.8 L/kg Compound A.

In reactor A of each experiment a certain fraction of the mother liquor volume was removed by distillation, either at atmospheric or reduced pressure (95-100° C. at atmospheric pressure, 55-60° C. under reduced pressure). In reactor B nothing was distilled off. The content of both reactors were then allowed to cool gradually to 15° C. over 10-12 hours before filtration, wash with methanol and drying under reduced pressure and elevated temperature. The purity of the crystals was measured by HPLC. The following results were obtained:

| | Water content in mother liquor, reactor A | Compound B purity, reactor A | Reduction of mother liquor volume, reactor A | Water content in mother liquor, reactor B | Compound B purity, reactor B | Reduction of mother liquor volume, reactor B | Isolated yield increase, reactor B vs. reactor A |
|---|---|---|---|---|---|---|---|
| 1 | 81% | 99.6% | 11% | 76% | 99.6% | None | 1.3% |
| 2 | 84% | 99.6% | 11% | 76% | 99.6% | None | 1.4% |
| 3 | 85% | 99.5% | 14% | 78% | 99.5% | None | 1.7% |
| 4 | 84% | 99.5% | 17% | 73% | 99.6% | None | 1.9% |
| 5 | 83% | 99.5% | 14% | 75% | 99.5% | None | 1.6% |
| 6 | 88% | 99.5% | 27% | 77% | 99.4% | None | 2.9% |
| 7 | 91% | 99.5% | 24% | 80% | 99.5% | None | 2.5% |
| 8 | 89% | 99.5% | 36% | 76% | 99.5% | None | 2.9% |
| 9 | 85% | 99.4% | 28% | 74% | 99.5% | None | 2.4% |
| 10 | 89% | 99.4% | 32% | 75% | 99.5% | None | 3.1% |

All patents, journal articles, publications and other documents discussed and/or cited above are hereby incorporated by reference.

We claim:

1. An improved process for the crystallisation of 5-acetamido-N,N'-bis(2,3-dihydroxypropyl)-2,4,6-triiodoisophthalamide (Compound A) in a mixture, comprising:
   a) providing crystalline Compound A in water and methanol; and
   b) reducing the volume percentage of methanol by evaporating methanol and water until said mixture comprises more than 75% (v/v) water and less than 25% (v/v) of methanol.

2. The process according to claim 1, wherein said mixture comprises more than about 80% (v/v) water and less than about 20% (v/v) methanol.

* * * * *